United States Patent [19]
Brockhaus et al.

[11] Patent Number: 5,808,029
[45] Date of Patent: Sep. 15, 1998

[54] DNA ENCODING A HUMAN TNF BINDING PROTEIN

[75] Inventors: Manfred Brockhaus, Bettingen; Zlatko Dembic, Basel, both of Switzerland; Reiner Gentz, Rheinfelden, Germany; Werner Lesslauer, Basel; Hansruedi Lötscher, Möhlin, both of Switzerland; Ernst-Jürgen Schlaeger, Efringen-Kirchen, Germany

[73] Assignee: Hoffmann-La Roche Inc., Nutley, N.J.

[21] Appl. No.: 444,793

[22] Filed: May 19, 1995

Related U.S. Application Data

[62] Division of Ser. No. 95,640, Jul. 21, 1993, Pat. No. 5,610,279, which is a continuation of Ser. No. 580,013, Sep. 10, 1990, abandoned.

[30] Foreign Application Priority Data

| Sep. 12, 1989 | [CH] | Switzerland | 3319/89 |
| Mar. 8, 1990 | [CH] | Switzerland | 746/90 |
| Apr. 20, 1990 | [CH] | Switzerland | 1347/90 |

[51] Int. Cl.$^6$ .......................... C12N 15/12; C07K 14/715
[52] U.S. Cl. .......................... 536/23.5; 435/69.1
[58] Field of Search .................................. 536/27, 23.53, 536/23.42, 23.5; 435/69.7, 70.21; 530/388.22, 387.1, 866, 867, 391.1, 395

[56] References Cited

U.S. PATENT DOCUMENTS

| 4,770,995 | 9/1988 | Rubin et al. . | |
| 4,816,567 | 3/1989 | Cabilly et al. . | |
| 4,948,875 | 8/1990 | Tanaka et al. . | |
| 5,116,964 | 5/1992 | Capon et al. . | |
| 5,359,037 | 10/1994 | Wallach et al. | 530/388.22 |
| 5,395,760 | 3/1995 | Smith et al. . | |

FOREIGN PATENT DOCUMENTS

| 308 378 | 3/1989 | European Pat. Off. . | |
| 325 224 | 7/1989 | European Pat. Off. . | |
| 393 438 | 4/1990 | European Pat. Off. . | |
| 0 422 339 A1 | 7/1990 | European Pat. Off. . | |
| 398 327 | 11/1990 | European Pat. Off. . | |
| 464 533 | 1/1991 | European Pat. Off. . | |
| 412 486 | 2/1991 | European Pat. Off. . | |
| 418 014 | 3/1991 | European Pat. Off. . | |
| 422 339 | 4/1991 | European Pat. Off. . | |
| 433 900 | 6/1991 | European Pat. Off. . | |
| 2218101 | 11/1989 | United Kingdom . | |
| 89/02922 | 6/1989 | WIPO | C12N 15/00 |
| 89/08114 | 8/1989 | WIPO | C07H 17/02 |
| 9013575 | 11/1990 | WIPO . | |
| 91/03553 | 3/1991 | WIPO . | |

OTHER PUBLICATIONS

Instructions to Authors, JBC 254(4):663 Jan. 5, 1989.
"Isolation and Characterization of a Tumor Necrosis Factor Binding Protein From Urine", Olsson et al, *Eur. J. Hematol.* (1989) 42:270–275.
English language abstract corresponding to WO 90/13575.
English language abstract corresponding to EP 393 438.

Proc. Natl. Acad. Sci. USA, vol. 87, pp. 3127–3131, Apr. 1990.
Gen Seq DBase Printout.
Stauber et al., "Human tumor necrosis factor–α receptor—purification by immunoaffinity chromatography and initial characterization", J. Bio. Chem. 263: 19098–19104 (1988).
Seckinger et al., "Purification and biologic characterization of a specific tumor necrosis factor α inhibitor", J. Bio. Chem. 264:11966–11973 (1989).
Engelmann et al., "A tumor necrosis factor–binding protein purified to homogeneity from human urine protects cells from tumor necrosis factor toxicity", J. Bio. Chem. 264:11974–11980 (1989).
Hohmann et al., "Two different cell types have different major receptors for human tumor necrosis factor (TNFα)", J. Bio. Chem. 264:14927–14934 (1989).
Smith et al., "A receptor for tumor necrosis factor defines an unusual family of cellular and viral proteins", Science 248:1119–1023 (1990).
Heller et al., "Complementary DNA cloning of a receptor for tumor necrosis factor and demonstration of a shed form of the receptor", Proc. Natl. Acad. Sci. U.S.A. 87:6151–6155 (1990).
Novick et al., "Soluble cytokine receptors are present in normal human urine", J. Exp. Med. 170:1409–1414 (1989).
Engelmann et al., "Two tumor necrosis factor–binding proteins purified from human urine", J. Bio. Chem. 265:1531–1536 (1990).
Schall et al., "Molecular cloning and expression of a receptor for human tumor necrosis factor", Cell 61:361–370 (1990).
Seckinger et al., "Tumor necrosis factor inhibitor: purification, $NH_2$–terminal amino acid sequence and evidence for anti–inflammatory and immunomodulatory activities", Eur. J. Immunol. 20:1167–1174 (1990).
Hohmann et al., "Expression of the types A and B tumor necrosis factor (TNT) receptors is independently regulated, and both receptors mediate activiation of the transcription factor NF–kB", J. Bio. Chem. 265:22409–22417 (1990).

(List continued on next page.)

*Primary Examiner*—David L. Fitzgerald
*Assistant Examiner*—Daryl A. Basham
*Attorney, Agent, or Firm*—George W. Johnston; William H. Epstein; John P. Parise

[57] ABSTRACT

The present invention is concerned with non-soluble proteins and soluble or insoluble fragments thereof, which bind TNF, in homogeneous form, as well as their physiologically compatible salts, especially those proteins having a molecular weight of about 55 or 75 kD (non-reducing SDS-PAGE conditions), a process for the isolation of such proteins, antibodies against such proteins, DNA sequences which code for non-soluble proteins and soluble or non-soluble fragments thereof, which bind TNF, as well as those which code for proteins comprising partly of a soluble fragment, which binds TNF, and partly of all domains except the first of the constant region of the heavy chain of human immunoglobulins and the recombinant proteins coded thereby as well as a process for their manufacture using transformed pro- and eukaryotic host cells.

1 Claim, 6 Drawing Sheets

OTHER PUBLICATIONS

Espevik et al., "Characterization of binding and biological effects of monoclonal antibodies against a human tumor necrosis factor receptor", J. Exp. Med. 171:415–426 (1990).

Porteu and Nathan, "Shedding of tumor necrosis factor receptors by activated human neutrophils", J. Exp. Med. 172:599–607 (1990).

Engelmann et al., "Antibodies to a soluble form of a tumor necrosis factor (TNF) receptor have TNF–like activity", J. Bio. Chem. 265:14497–14504 (1990).

Seckinger et al., "Characterization of a tumor necrosis factor α (TNF–α) inhibitor: evidence of immunological cross–activity with the TNF receptor;", Proc. Natl. Sci. USA 87:5188–5192 (1990).

Gray et al., "Cloning of human tumor necrosis factor (TNF) receptor cDNA and expression of recombinant soluble TNF–binding protein", Proc. Natl. Sci. USA 87:7380–7384 (1990).

Loetscher et al., "Molecular cloning and expression of the human 55 kd tumor necrosis factor receptor", Cell 61:351–359 (1990).

Peppel et al., "Chimaeric TNF–receptor—IgG molecule acts as soluble inhibitor of TNF mediated cytotoxicity", Journal of Cellular Biochem., Abstract, 20th Annual Meetings, Keystone Symposia on Molecular and Cellular Biology, p. 118, Supplement 15F (1991).

Olsson et al., "Isolation and characterization of a tumor necrosis factor binding protein from urine", Eur. J. Haematol. 42:270–275 (1989).

Capon et al., "Designing CD4 immunoadhesins for AIDS therapy", Nature 337:525–530 (Feb. 9, 1989).

Abstract 92–009794/02 (1992) for EP 464 533.

```
-185  GAATTCGGGGGGGTTCAAGATCACTGGGACCAGGCCGTGATCTCTATGCCCGAGTCTCAA
-125  CCCTCAACTGTCACCCCAAGGCACTTGGGACGTCCTGGACAGACCGAGTCCCGGGAAGCC
 -65  CCAGCACTGCCGCTGCCACACTGCCCTGAGCCCAAATGGGGGAGTGAGAGGCCATAGCTG
           -28.
 -30         MetGlyLeuSerThrValProAspLeuLeuLeuProLeuValLeuLeuGluLeu
  -5  TCTGGCATGGGCCTCTCCACCGTGCCTGACCTGCTGCTGCCGCTGGTGCTCCTGGAGCTG
                                                               +1
 -10  LeuValGlyIleTyrProSerGlyValIleGlyLeuValProHisLeuGlyAspArgGlu
  55  TTGGTGGGAATATACCCCTCAGGGGTTATTGGACTGGTCCCTCACCTAGGGGACAGGGAG
                                                             ***
  10  LysArgAspSerValCysProGlnGlyLysTyrIleHisProGlnAsnAsnSerIleCys
 115  AAGAGAGATAGTGTGTGTCCCCAAGGAAAATATATCCACCCTCAAAATAATTCGATTTGC

30  CysThrLysCysHisLysGlyThrTyrLeuTyrAsnAspCysProGlyProGlyGlnAsp
 175  TGTACCAAGTGCCACAAAGGAACCTACTTGTACAATGACTGTCCAGGCCCGGGGCAGGAT

50  ThrAspCysArgGluCysGluSerGlySerPheThrAlaSerGluAsnHisLeuArgHis
 235  ACGGACTGCAGGGAGTGTGAGAGCGGCTCCTTCACCGCTTCAGAAAACCACCTCAGACAC

70  CysLeuSerCysSerLysCysArgLysGluMetGlyGlnValGluIleSerSerCysThr
 295  TGCCTCAGCTGCTCCAAATGCCGAAAGGAAATGGGTCAGGTGGAGATCTCTTCTTGCACA

90  ValAspArgAspThrValCysGlyCysArgLysAsnGlnTyrArgHisTyrTrpSerGlu
 355  GTGGACCGGGACACCGTGTGTGGCTGCAGGAAGAACCAGTACCGGCATTATTGGAGTGAA
                     ***                                 ***
 110  AsnLeuPheGlnCysPheAsnCysSerLeuCysLeuAsnGlyThrValHisLeuSerCys
 415  AACCTTTTCCAGTGCTTCAATTGCAGCCTCTGCCTCAATGGGACCGTGCACCTCTCCTGC

130  GlnGluLysGlnAsnThrValCysThrCysHisAlaGlyPhePheLeuArgGluAsnGlu
 475  CAGGAGAAACAGAACACCGTGTGCACCTGCCATGCAGGTTTCTTTCTAAGAGAAAACGAG

150  CysValSerCysSerAsnCysLysLysSerLeuGluCysThrLysLeuCysLeuProGln
 535  TGTGTCTCCTGTAGTAACTGTAAGAAAAGCCTGGAGTGCACGAAGTTGTGCCTACCCCAG

170  IleGluAsnValLysGlyThrGluAspSerGlyThrThrValLeuLeuProLeuValIle
 595  ATTGAGAATGTTAAGGGCACTGAGGACTCAGGCACCACAGTGCTGTTGCCCCTGGTCATT

190  PhePheGlyLeuCysLeuLeuSerLeuLeuPheIleGlyLeuMetTyrArgTyrGlnArg
 655  TTCTTTGGTCTTTGCCTTTTATCCCTCCTCTTCATTGGTTTAATGTATCGCTACCAACGG

210  TrpLysSerLysLeuTyrSerIleValCysGlyLysSerThrProGluLysGluGlyGlu
 715  TGGAAGTCCAAGCTCTACTCCATTGTTTGTGGGAAATCGACACCTGAAAAGAGGGGGAG
                                                             ***
 230  LeuGluGlyThrThrThrLysProLeuAlaProAsnProSerPheSerProThrProGly
 775  CTTGAAGGAACTACTACTAAGCCCCTGGCCCCAAACCCAAGCTTCAGTCCCACTCCAGGC

250  PheThrProThrLeuGlyPheSerProValProSerSerThrPheThrSerSerSerThr
 835  TTCACCCCCACCCTGGGCTTCAGTCCCGTGCCCAGTTCCACCTTCACCTCCAGCTCCACC
```

FIG. 1A

| | |
|---|---|
| 270 | PheThrProThrLeuGlyPheSerProValProSerSerThrPheThrSerSerSerThr |
| 895 | TATACCCCCGGTGATGTCCCAACTTTGCTGGCTCCCCGCAGAGAGGTGGCACCACCCTAT |
| 290 | GlnGlyAlaAspProIleLeuAlaThrAlaLeuAlaSerAspProIleProAsnProLeu |
| 955 | CAGGGGGCTGACCCCATCCTTGCGACAGCCCTCGCCTCCGACCCCATCCCCAACCCCCTT |
| 310 | GlnLystrpGluAspSerAlaHisLysProGlnSerLeuAspThrAspAspProAlaThr |
| 1015 | CAGAAGTGGGAGGACAGCGCCCACAAGCCACAGAGCCTAGACACTGATGACCCCGCGACG |
| 330 | LeuTyrAlaValValGluAsnValproProLeuArgTrpLysGluPheValArgArgLeu |
| 1075 | CTGTACGCCGTGGTGGAGAACGTGCCCCCGTTGCGCTGGAAGGAATTCGTGCGGCGCCTA |
| 350 | GlyLeuSerAspHisGluIleAspArgLeuGluLeuGlnAsnGlyArgCysLeuArgGlu |
| 1135 | GGGCTGAGCGACCACGAGATCGATCGGCTGGAGCTGCAGAACGGGCGCTGCCTGCGCGAG |
| 370 | AlaGlnTyrSerMetLeuAlaThrTrpArgArgArgThrProArgArgGluAlaThrLeu |
| 1195 | GCGCAATACAGCATGCTGGCGACCTGGAGGCGGCGCACGCCGCGGCGCGAGGCCACGCTG |
| 390 | GluLeuLeuGlyArgValLeuArgAspMetAspLeuLeuGlyCysLeuGluAspIleGlu |
| 1255 | GAGCTGCTGGGACGCGTGCTCCGCGACATGGACCTGCTGGGCTGCCTGGAGGACATCGAG |
| 410 | GluAlaLeuCysGlyProAlaAlaLeuProProAlaProSerLeuLeuArg |
| 1315 | GAGGCGCTTTGCGGCCCCGCCGCCCTCCCGCCCGCGCCCAGTCTTCTCAGATGAGGCTGC |
| 1375 | GCCCCTGCGGGCAGCTCTAAGGACCGTCCTGCGAGATCGCCTTCCAACCCCACTTTTTTC |
| 1435 | TGGAAAGGAGGGGTCCTGCAGGGGCAAGCAGGAGCTAGCAGCCGCCTACTTGGTGCTAAC |
| 1495 | CCCTCGATGTACATAGCTTTTCTCAGCTGCCTGCGCGCCGCCGACAGTCAGCGCTGTGCG |
| 1555 | CGCGGAGAGAGGTGCGCCGTGGGCTCAAGAGCCTGAGTGGGTGGTTTGCGAGGATGAGGG |
| 1615 | ACGCTATGCCTCATGCCCGTTTTGGGTGTCCTCACCAGCAAGGCTGCTCGGGGGCCCCTG |
| 1675 | GTTCGTCCCTGAGCCTTTTTCACAGTGCATAAGCAGTTTTTTTTGTTTTTGTTTTGTTTT |
| 1735 | GTTTTGTTTTTAAATCAATCATGTTACACTAATAGAAACTTGGCACTCCTGTGCCCTCTG |
| 1795 | CCTGGACAAGCACATAGCAAGCTGAACTGTCCTAAGGCAGGGGCGAGCACGGAACAATGG |
| 1855 | GGCCTTCAGCTGGAGCTGTGGACTTTTGTACATACACTAAAATTCTGAAGTTAAAAAAAA |
| 1915 | AACCCGAATTC |

*FIG. 1B*

```
  1    SerAspSerValCysAspSerCysGluAspSerThrTyrThrGlnLeuTrpAsnTrpVal
  1    TCGGACTCCGTGTGTGACTCCTGTGAGGACAGCACATACACCCAGCTCTGGAACTGGGTT

21    ProGluCysLeuSerCysGlySerArgCysSerSerAspGlnValGluThrGlnAlaCys
 61    CCCGAGTGCTTGAGCTGTGGCTCCCGCTGTAGCTCTGACCAGGTGGAAACTCAAGCCTGC

41    ThrArgGluGlnAsnArgIleCysThrCysArgProGlyTrpTyrCysAlaLeuSerLys
121    ACTCGGGAACAGAACCGCATCTGCACCTGCAGGCCCGGCTGGTACTGCGCGCTGAGCAAG

61    GlnGluGlyCysArgLeuCysAlaProLeuProLysCysArgProGlyPheGlyValAla
181    CAGGAGGGGTGCCGGCTGTGCGCGCCGCTGCCGAAGTGCCGCCCGGGCTTCGGCGTGGCC

81    ArgProGlyThrGluThrSerAspValValCyslysProCysAlaProGlyThrPheSer
241    AGACCAGGAACTGAAACATCAGACGTGGTGTGCAAGCCCTGTGCCCCGGGGACGTTCTCC 101    AsnThrThrSerSerThrAspIleCysArgProHisGlnIleCysAsnValValAlaIle
301    AACACGACTTCATCCACGGATATTTGCAGGCCCCACCAGATCTGTAACGTGGTGGCCATC 121    ProGlyAsnAlaSerArgAspAlaValCysThrSerThrSerProThrArgSerMetAla
361    CCTGGGAATGCAAGCAGGGATGCAGTCTGCACGTCCACGTCCCCCACCCGGAGTATGGCC 141    ProGlyAlaValHisLeuProGlnProValSerThrArgSerGlnHisThrGlnProSer
421    CCAGGGGCAGTACACTTACCCCAGCCAGTGTCCACACGATCCCAACACACGCAGCCAAGT 161    ProGluProSerThrAlaProSerThrSerPheLeuLeuProMetGlyProSerProPro
481    CCAGAACCCAGCACTGCTCCAAGCACCTCCTTCCTGCTCCCAATGGGCCCCAGCCCCCCA 181    AlaGluGlySerThrGlyAspPheAlaLeuProValGlyLeuIleValGlyValThrAla
541    GCTGAAGGGAGCACTGGCGACTTCGCTCTTCCAGTTGGACTGATTGTGGGTGTGACAGCC 201    LeuGlyLeuLeuIleIleGlyValValAsnCysValIleMetThrGlnValLysLysLys
601    TTGGGTCTACTAATAATAGGAGTGGTGAACTGTGTCATCATGACCCAGGTGAAAAGAAG 221    ProLeuCysLeuGlnArgGluAlaLysValProHisLeuProAlaAspLysAlaArgGly
661    CCCTTGTGCCTGCAGAGAGAAGCCAAGGTGCCTCACTTGCCTGCCGATAAGGCCCGGGGT 241    ThrGlnGlyProGluGlnGlnHisLeuLeuIleThrAlaProSerSerSerSerSerSer
721    ACACAGGGCCCCGAGCAGCAGCACCTGCTGATCACAGCGCCGAGCTCCAGCAGCAGCTCC 261    LeuGluSerSerAlaSerAlaLeuAspArgArgAlaProThrArgAsnGlnProGlnAla
781    CTGGAGAGCTCGGCCAGTGCGTTGGACAGAAGGGCGCCCACTCGGAACCAGCCACAGGCA
```

*FIG. 4A*

```
281  ProGlyValGluAlaSerGluAlaGlyGluAlaArgAlaSerThrGlySerSerAlaAsp
841  CCAGGCGTGGAGGCCAGTGGGGCCGGGGAGGCCCGGGCCAGCACCGGGAGCTCAGCAGAT

301  SerSerProGlyGlyHisGlyThrGlnValAsnValThrCysIleValAsnValCysSer
901  TCTTCCCCTGGTGGCCATGGGACCCAGGTCAATGTCACCTGCATCGTGAACGTCTGTAGC

321  SerSerAspHisSerSerGlnCysSerSerGlnAlaSerSerThrMetGlyAspThrAsp
961  AGCTCTGACCACAGCTCACAGTGCTCCTCCCAAGCCAGCTCCACAATGGGAGACACAGAT

341  SerSerProSerGluSerProLysAspGluGlnValProPheSerLysGluGluCysAla
1021 TCCAGCCCCTCGGAGTCCCCGAAGGACGAGCAGGTCCCCTTCTCCAAGGAGGAATGTGCC

361  PheArgSerGlnLeuGluThrProGluThrLeuLeuGlySerThrGluGluLysProLeu
1081 TTTCGGTCACAGCTGGAGACGCCAGAGACCCTGCTGGGGAGCACCGAAGAGAAGCCCCTG

381  ProLeuGlyValProAspAlaGlyMetLysProSer
1141 CCCCTTGGAGTGCCTGATGCTGGGATGAAGCCCAGTTAACCAGGCCGGTGTGGGCTGTGT
1201 CGTAGCCAAGGTGGCTGAGCCCTGGCAGGATGACCCTGCGAAGGGGCCCTGGTCCTTCCA
1261 GGCCCCCACCACTAGGACTCTGAGGCTCTTTCTGGGCCAAGTTCCTCTAGTGCCCTCCAC
1321 AGCCGCAGCCTCCCTCTGACCTGCAGGCCAAGAGCAGAGGCAGCGAGTTGTGGAAAGCCT
1381 CTGCTGCCATGGCGTGTCCCTCTCGGAAGGCTGGCTGGGCATGGACGTTCGGGGCATGCT
1441 GGGGCAAGTCCCTGAGTCTCTGTGACCTGCCCCGCCCAGCTGCACCTGCCAGCCTGGCTT
1501 CTGGAGCCCTTGGGTTTTTTGTTTGTTTGTTTGTTTGTTTGTTTCTCCCCTGGGC
1561 TCTGCCCAGCTCTGGCTTCCAGAAAACCCCAGCATCCTTTTCTGCAGAGGGGCTTTCTGG
1621 AGAGGAGGGATGCTGCCTGAGTCACCCATGAAGACAGGACAGTGCTTCAGCCTGAGGCTG
1681 AGACTGCGGGATGGTCCTGGGGCTCTGTGCAGGGAGGAGGTGGCAGCCCTGTAGGGAACG
1741 GGGTCCTTCAAGTTAGCTCAGGAGGCTTGGAAAGCATCACCTCAGGCCAGGTGCAGTGGC
1801 TCACGCCTATGATCCCAGCACTTTGGGAGGCTGAGGCGGGTGGATCACCTGAGGTTAGGA
1861 GTTCGAGACCAGCCTGGCCAACATGGTAAAACCCCATCTCTACTAAAAATACAGAAATTA
1921 GCCGGGCGTGGTGGCGGGCACCTATAGTCCCAGCTACTCAGAAGCCTGAGGCTGGGAAAT
2041 TGGGCGACAGAGCGAGAGTCTGTCTCAAAAGAAAAAAAAAAGCACCGCCTCCAAATGCT
2101 AACTTGTCCTTTTGTACCATGGTGTGAAAGTCAGATGCCCAGAGGGCCCAGGCAGGCCAC
2161 CATATTCAGTGCTGTGGCCTGGGCAAGATAACGCACTTCTAACTAGAAATCTGCCAATTT
2221 TTTAAAAAGTAAGTACCACTCAGGCCAACAAGCCAACGACAAAGCCAAACTCTGCCAGC
2281 CACATCCAACCCCCCACCTGCCATTTGCACCCTCCGCCTTCACTCCGGTGTGCCTGCAG
```

*FIG. 4B*

DNA ENCODING A HUMAN TNF BINDING PROTEIN

This is a division of application Ser. No. 08/095,640, filed Jul. 21, 1993 now U.S. Pat. No. 5,610,279), which is a continuation application of Ser. No. 07/580,013, filed Sep. 10, 1990 (now abandoned); and amend the claims pursuant to the Preliminary Amendment submitted concurrently herewith.

BACKGROUND OF THE INVENTION

Tumor necrosis factor a (TNFα, also cachectin), discovered as a result of its haemorragic-necrotizing activity on certain tumors, and lymphotoxin (TNFβ) are two closely related peptide factors [3] from the class of lymphokines/cytokines which are both referred to hereinafter as TNF [see references 2 and 3]. TNF possesses a broad cellular spectrum of activity. For example, TNF has inhibitory or cytotoxic activity on a series of tumor cell lines [2, 3], stimulates the proliferation of fibroblasts and the phagocytic/cytotoxic activity of myeloic cells [4, 5, 6], induces adhesion molecules in endothelial cells or exerts an inhibitory activity on the endothelium [7, 8, 9, 10], inhibits the synthesis of specific enzymes in adipocytes [11] and induces the expression of histo-compatibility antigens [12]. Many of these TNF activities are produced via induction of other factors or by synergistic effects with other factors such as interferons or interleukins [13–16].

TNF is involved in pathological conditions such as shock states in meningococcal sepsis [17], the development of autoimmune glomerulonephritis in mice [18] and cerebral malaria in mice [19] and human beings [41]. The toxic effects of endotoxin appear to be mediated by TNF [20]. Furthermore, TNF can trigger interleukin-1 fever [39]. On the basis of its pleiotropic functional properties, TNF in interaction with other cytokines is involved in additional pathological conditions as a mediator of immune response, inflammation, and other processes.

These biological effects are mediated by TNF via specific receptors. According to present knowledge not only TNFα, but also TNFβ bind to the same receptors [21]. Different cell types differ in their number of TNF receptors [22, 23, 24]. Generally known TNF-binding proteins (TNF-BP) have been detected by covalent bonding to radioactively labelled TNF [24–29], and the following apparent molecular weights of the TNF/TNF-BP complexes obtained have been determined to be: 95/100 kD and 75 kD [24], 95 kD and 75 kD [25], 138 kD, 90 kD, 75 kD and 54 kD [26], 100±5 kD [27], 97 kD and 70 kD [28] and 145 kD [29]. One such TNF/TNF-BP complex was isolated by anti-TNF-antibody immune affinity chromatography and preparative SDS-polyacrylamide gel electrophoreses (SDS-PAGE) [27]. The reductive cleavage of this complex and subsequent SDS-PAGE analysis gave several bands which were not tested for TNF-binding activity. Since the specific conditions which must be used for the cleavage of the complex lead to inactivation of the binding protein [31], the latter has also not been possible. The separation of soluble TNF-BP from human serum or urine by ion exchange chromatography and gel filtration (molecular weight in the region of 50 kD) was described by Olsson et al. [30].

Brockhaus et al. [32] obtained an enriched TNF-BP preparation from membrane extracts of $HL_{60}$ cells by TNFα-ligand affinity chromatography and HPLC which, in turn, was used as an antigen preparation for the production of monoclonal antibodies against TNF-BP. Using such an immobilized antibody (immune affinity chromatography) Loetscher and Brockhaus obtained an enriched preparation of TNF-BP [31] from an extract of human placenta using TNFα-ligand affinity chromatography and HPLC, which gave a strong broad band at 35 kD, a weak band at about 40 kD and a very weak band in the region between 55 kD and 60 kD on SDS-PAGE analysis. Moreover, the gel showed a protein background smear in the region of 33 kD to 40 kD. The significance of these protein bands was, however, not clear due to the heterogenicity of the starting material which was used (placenta tissue; combined material from several placentas). In the state of the art TNF-BP have already been characterized by a N-terminal partial sequence [European Patent Application, Publication No. 308 378], whereby this sequence differs from the N-terminal partial sequence according to formula (IA) in accordance with the invention. Moreover, the TNF-binding proteins described in the state of the art are soluble, i.e. non-membrane bound, TNF-BP and not membrane-bound, i.e. insoluble, TNF-BP isolated from urine.

SUMMARY OF THE INVENTION

This invention comprises insoluble, homogenous proteins or soluble or insoluble fragments thereof, capable of binding tumor necrosis factor-(TNF).

This invention also comprises TNF-binding proteins containing amino acid sequences of FIG. 1 or FIG. 4, proteins containing fragments of these sequences, and proteins analagous to the sequences of FIG. 1 or FIG. 4 or to fragments thereof.

This invention further comprises DNA sequences encoding the proteins described above, proteins encoded by these sequences, and antibodies to any of these proteins.

This invention comprises DNA sequences which combine two partial DNA sequences, one sequence encoding soluble fragments of TNF binding proteins and the other partial sequence encoding all domains except the first domain of the constant region of the heavy chain of human immunoglobulin IgG, IgA, IgM, or IgE, and the recombinant proteins encoded by these sequences.

This invention additionally comprises vectors containing the above DNA sequences, and host systems transfected with such vectors.

This invention finally comprises a process for the isolation of an insoluble homogenous protein capable of binding TNF.

BRIEF DESCRIPTION OF THE FIGURES

FIG. 1. Nucleotide sequence and deduced amino acid sequence for cDNA clone derived from 55 kD TNF-BP. The 19 amino acid transmembrane region is underlined. Hypothetical glycosylation sites are identified by asterisks.

FIG. 4. Nucleotide sequence and deduced amino acid sequence for cDNA clones derived from 75/65 kD TNF-BP.

DETAILED DESCRIPTION OF THE INVENTION

Figure 2A:
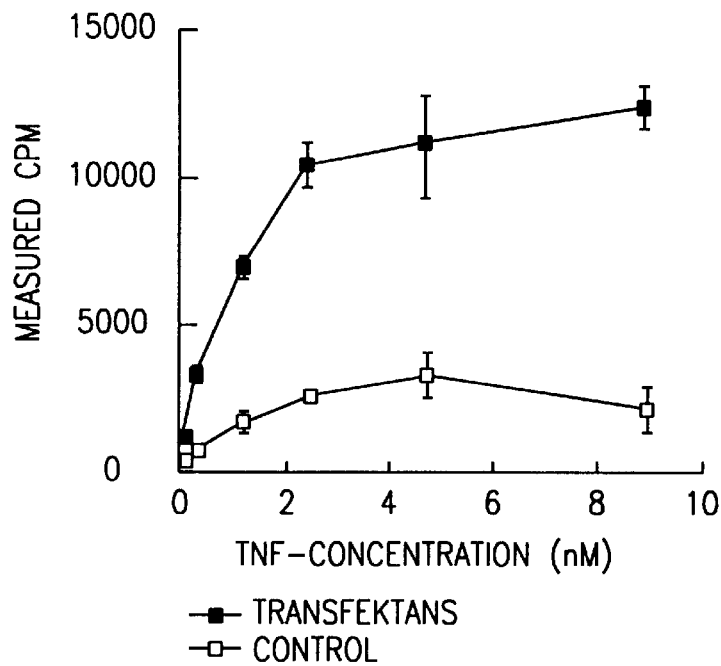
FIGS. 2A and 2B Binding analysis of COS cells transfected with plasmid pN123. Panel 2A -binding of transfected cells to $^{125}$I-TNFα. Panel 2B -Scatchard plot of binding data.

The TNF-binding proteins of the present invention are homogenous, insoluble proteins and soluble or insoluble fragments of such proteins which are capable of binding TNF. These proteins have the ability to bind TNF as measured by standard assays.

The TNF-binding proteins of the present invention include homogenous proteins containing the amino acid sequence depicted in FIG. 1 or in FIG. 4, proteins containing fragments of either sequence, and analogues of any such proteins for example proteins containing amino acid sequences analogous to the amino acid sequences of FIG. 1 or FIG. 4 or to fragments thereof. An analogue is a protein in which one or more amino acids of the sequences depicted in FIG. 1 or in FIG. 4 have had their side-groups chemically modified in a known manner, or those in which one or more amino acids have been replaced or deleted, without thereby eliminating TNF-binding ability. Such analogues may be produced by known methods of peptide chemistry, or by known methods of recombinant DNA technology, such as planned mutagenesis.

The TNF binding activity of the proteins of the present invention may be determined using the assay described in Example 1.

TNF-binding proteins of this invention are obtained as follows:

TNF binding proteins may be isolated from tissues and purified to homogeneity, or isolated from cells which contain membrane-bound TNF binding protein, and purified to homogeneity. One possible method for growing cells and isolating cell extract is described in Example 2, however, other cells types and other growth and isolation methods are well known in the art. Purification of TNF-binding proteins from cell extracts may be performed using the methods described in Examples 4, 5, and 6 in combination with the assay described in Example 1. TNF-binding proteins isolated and purified by these methods were sequenced by well-known methods, as described in Example 7. From these amino acid sequences, DNA probes were produced and used to obtain mRNA encoding TNF binding proteins from which cDNA was made, all by known methods described in Examples 8 and 11. Other well-known methods for producing cDNA are known in the art and may effectively be used. In general, any TNF-binding protein can be isolated from any cell or tissue expressing such proteins using a cDNA probe such as the probe described above, isolating mRNA and transcribing the mRNA into cDNA. Thereafter, the protein can be produced by inserting the cDNA into an expression vector as described in Example 9, such as a virus, plasmid, cosmid, or other vector, inserting the expression vector into a cell, such as the COS cell described in Example 9 or the insect cell described in Example 10, proliferating the resulting cells, and isolating the expressed TNF-binding protein from the medium or from cell extract as described above. Alternatively, TNF-binding proteins may be chemically synthesized using the sequence described above and an amino acid synthesizer, or manual synthesis using chemical conditions well known to form peptide bonds between selected amino acids. Analogues and fragments of TNF-binding proteins may be produced by the above methods. In the case of analogues. the proteins may be chemically modified, or modified by genetic engineering as described above. These fragments and analogues may then be tested for TNF-binding activity using methods such as the assay of Example 1.

Finally, monoclonal antibodies directed against TNF-binding proteins, such as the antibodies described in Example 3, may be produced by known techniques, and used to isolate TNF-binding proteins.

In more detail, the proteins of the present invention are non-soluble proteins, i.e. for example membrane proteins or so-called receptors, and soluble or non-soluble fragments thereof, which bind TNF (TNF-BP), in homogeneous form, as well as their physiologically compatible salts. Preferred proteins are those which according to SDS-PAGE under non-reducing conditions are characterized by apparent molecular weights of about 55 kD, 51 kD, 38 kD, 36 kD and 34 kD or 75 kD and 65 kD, especially those with about 55 kD and 75 kD. Furthermore, there are preferred those proteins which are characterized by containing at least one of the following amino acid partial sequences:

(IA) Leu-Val-Pro-His-Leu-Gly-Asp-Arg-Glu-Lys-Arg-Asp-Ser-Val-Cys-Pro-Gln-Gly-Lys-Tyr-Ile-His-Pro-Gln-X-Asn-Ser-Ile (IB) Ser-Thr-Pro-Glu-Lys-Glu-Gly-Glu-Leu-Glu-Gly-Thr-Thr-Thr-Lys (IIA) Ser-Gln-Leu-Glu-Thr-Pro-Glu-Thr-Leu-Leu-Gly-Ser-Thr-Glu-Glu-Lys-Pro-Leu (IIB) Val-Phe-Cys-Thr (IIC) Asn-Gln-Pro-Gln-Ala-Pro-Gly-Val-Glu-Ala-Ser-Gly-Ala-Gly-Glu-Ala (IID) Leu-Pro-Ala-Gln-Val-Ala-Phe-X-Pro-Tyr-Ala-Pro-Glu-Pro-Gly-Ser-Thr-Cys (IIE) Ile-X-Pro-Gly-Phe-Gly-Val-Ala-Tyr-Pro-Ala-Leu-Glu (IIF) Leu-Cys-Ala-Pro (IIG) Val-Pro-His-Leu-Pro-Ala-Asp (IIH) Gly-Ser-Gln-Gly-Pro-Glu-Gln-Gln-X-X-Leu-Ile-X-Ala-Pro in which X stands for an amino acid residue which could not be unequivocally determined.

A process for the isolation of the TNF-BP in accordance with the invention is also an object of the present invention. This process comprises carrying out essentially the following purification steps in sequence: production of a cell or tissue extract, immune affinity chromatography and/or single or multiple ligand affinity chromatography, high resolution liquid chromatography (HPLC) and preparative SDS-polyacrylamide gel electrophoresis (SDS-PAGE). The combination of the individual purification steps, which are known from the state of the art, is essential to the success of the process in accordance with the invention, whereby individual steps have been modified and improved having regard to the problem to be solved. Thus, for example, the original combined immune affinity chromatography/TNFα-ligand affinity chromatography step originally used for the enrichment of TNF-BP from human placenta [31] has been altered by using a BSA-Sepharose 4B pre-column. For the application of the cell or membrane extract, this pre-column was connected in series with the immune affinity column followed by the ligand affinity column. After the application of the extract the two aforementioned columns were coupled, each eluted and the TNF-BP-active fractions were purified again via a ligand affinity column. The use of a detergent-containing solvent mixture for the performance of the reversed-phase HPLC step is essential to the invention.

Further, an industrial process for the production of high cell densities of mammalian cells from which TNF-BP can be isolated is also an object of the present invention. Such a process comprises using a medium, which has been developed for the specific growth requirements of the cell line used, in combination with a perfusion apparatus as described e.g. in detail in Example 2. By means of such a process there can be produced, for example, in the case of HL-60 cells up to more than 20-fold higher cell densities than usual.

In addition thereto, the present invention is also concerned with DNA sequences coding for proteins and soluble or non-soluble fragments thereof, which bind TNF. Thereunder there are to be understood, for example, DNA sequences coding for non-soluble proteins or soluble as well as non-soluble fragments thereof, which bind TNF, such DNA sequences being selected from the following:

(a) DNA sequences as given FIG. 1 or FIG. 4 as well as their complementary strands, or those which include these sequences;

(b) DNA sequences which hybridize with sequences defined under (a) or fragments thereof;

(c) DNA sequences which, because of the degeneracy of the genetic code, do not hybridize with sequences as defined under (a) and (b), but which code for polypeptides having exactly the same amino acid sequence.

That is to say, the present invention embraces not only allelic variants, but also those DNA sequences which result from deletions, substitutions and additions from one or more nucleotides of the sequences given in FIG. 1 or FIG. 4, whereby in the case of the proteins coded thereby there come into consideration, just as before, TNF-BP. One sequence which results from such a deletion is described, for example, in Science 248, 1019–1023, (1990).

There are preferred first of all those DNA sequences which code for such a protein having an apparent molecular weight of about 55 kD, whereby the sequence given in FIG. 1 is especially preferred, and sequences which code for non-soluble as well as soluble fragments of such proteins. A DNA sequence which codes, for example, for such a non-soluble protein fragment extends from nucleotide −185 to 1122 of the sequence given in FIG. 1. DNA sequences which code for soluble protein fragments are, for example, those which extend from nucleotide −185 to 633 or from nucleotide −14 to 633 of the sequence given in FIG. 1. There are also preferred DNA sequences which code for a protein of about 75/65 kD, whereby those which contain the partial cDNA sequences shown in FIG. 4 are preferred. Especially preferred DNA sequences in this case are the sequences of the open reading frame of nucleotide 2 to 1,177. The peptides IIA, IIC, IIE, IIF, IIG and IIH are coded by the partial CDNA sequence in FIG. 4, whereby the insignificant deviations in the experimentally determined amino acid sequences are based on the cDNA-derived sequence with highest probability from the limited resolution of the gas phase sequencing. DNA sequences which code for insoluble as well as soluble fractions of TNF-binding proteins having an apparent molecular weight of 65 kD/75 kD are also preferred. DNA sequences for such soluble fragments can be determined on the basis of the amino acid sequences derived from the nucleic acid sequences coding for such non-soluble TNF-BP.

The invention is also concerned with DNA sequences which comprise a combination of two partial DNA sequences, with one of the partial sequences coding for those soluble fragments of non-soluble proteins which bind TNF (see above) and the other partial sequence coding for all domains other than the first domain of the constant region of the heavy chain of human immunoglobulins such as IgG, IgA, IgM or IgE, in particular $IgG_1$ or $IgG_3$ subtypes.

The present invention is also concerned with the recombinant proteins coded by any of DNA sequences described above. Of course, there are thereby also included such proteins in whose amino acid sequences amino acids have been exchanged, for example by planned mutagenesis, so that the activity of the TNF-BP or fragments thereof, namely the binding of TNF or the interaction with other membrane components participating in the signal transfer, have been altered or maintained in a desirable manner. Amino acid exchanges in proteins and peptides which do not generally alter the activity of such molecules are known in the state of the art and are described, for example, by H. Neurath and R. L. Hill in "The Proteins" (Academic Press, New York, 1979, see especially FIG. 6, page 14). The most commonly occurring exchanges are: Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, Asp/Gly as well as these in reverse. The present invention is also concerned with vectors which contain any of the DNA sequences described above in accordance with the invention and which are suitable for the transformation of suitable pro- and eukaryotic host systems, whereby there are preferred those vectors whose use leads to the expression of the proteins which are coded by any of the DNA sequences described above in accordance with the invention. Finally, the present invention is also concerned with pro- and eukaryotic host systems transformed with such vectors, as well as a process for the production of recombinant compounds in accordance with the invention by cultivating such host systems and subsequently isolating these compounds from the host systems themselves or their culture supernatants.

An object of the present invention are also pharmaceutical preparations which contain at least one of these TNF-BPs or fragments thereof, if desired in combination with other pharmaceutically active substances and/or non-toxic, inert, therapeutically compatible carrier materials.

Finally, the present invention is concerned with the use of such a TNF-BP on the one hand for the production of pharmaceutical preparations and on the other hand for the treatment of illnesses, preferably those in which TNF is involved in their course.

Starting materials for the TNF-BP in accordance with the invention are quite generally cells which contain such TNF-BP in membrane-bound form and which are generally accessible without restrictions to a person skilled in the art, such as, for example, HL60 [ATCC No. CCL 240], U 937 [ATCC No. CRL 1593], SW 480 [ATCC No. CCL 228] and HEp2 cells [ATCC No. CCL 23]. These cells can be cultivated according to known methods of the state of the art [40] or, in order to produce high cell densities, according to the procedure already described generally and described in detail in Example 2 for HL60 cells. TNF-BP can then be extracted from the cells, which are centrifuged-off from the medium and washed, according to known methods of the state of the art using suitable detergents, for example Triton X-114, 1-0-n-octyl-β-D-glucopyranoside (octylglucoside) or 3-[(3-cholylamidopropyl)-dimethylammonio]-1-propane sulphonate (CHAPS), especially using Triton X-100. For the detection of such TNF-BP there can be Used the usually used detection methods for TNF-BP, for example a polyethylene glycolinduced precipitation of the $^{125}$I-TNF/TNF-BP complex [27], especially filter-binding tests with radioactively labelled TNF according to Example 1. In order to produce the TNF-BP in accordance with the invention, the general methods of the state of the art used for the purification of proteins, especially of membrane proteins, such as, for is example, ion exchange chromatography, gel filtration, affinity chromatography, HPLC and SDS-PAGE can be used. Especially preferred methods for the production of TNF-BP in accordance with the invention are affinity chromatography, especially with TNF-α as the ligand bound to the solid phase, and immune affinity chromatography, HPLC and SDS-PAGE. The elution of TNF-BP bands which are separated using SDS-PAGE can be effected according to known methods of protein chemistry, for example using electroelution according to Hunkapiller et al. [34], whereby according to present knowledge the electro-dialysis times given there generally have to be doubled. Thereafter, traces of SDS which still remain can then be removed in accordance with Bosserhoff et al. [50].

The thus-purified TNF-BP can be characterized by methods of peptide chemistry which are known in the state of the art, such as, for example, N-terminal amino acid sequencing or enzymatic as well as chemical peptide cleavage. Fragments obtained by enzymatic or chemical cleavage can be separated according to usual methods such as, for example, HPLC and can themselves be subjected to further N-terminal sequencing. Such fragments which themselves bind TNF can be identified using the aforementioned detection methods for TNF-BP and are likewise objects of the present invention.

Starting from the thus-obtained amino acid sequence information or the DNA and amino acid sequences given in FIG. 1 as well as in FIG. 4 there can be produced, taking into consideration the degeneracy of the genetic code, according to methods known in the state of the art suitable oligonucleotides [51]. By means of these, again according to known methods of molecular biology [42, 43], cDNA or genomic DNA banks can be searched for clones which contain nucleic acid sequences coding for TNF-BP. Moreover, using the polymerase chain reaction (PCR) [49] cDNA fragments can be cloned by completely degenerating the amino acid sequence of two spaced apart relatively short segments while taking into consideration the genetic code and introducing into their complementarity suitable oligonucleotides as a "primer", whereby the fragment lying between these two sequences can be amplified and identified. The determination of the nucleotide sequence of a such a fragment permits an independent determination of the amino acid sequence of the protein fragment for which it codes. The cDNA fragments obtainable by PCR can also, as already described for the oligonucleotides themselves, be used according to known methods to search for clones containing nucleic acid sequences coding for TNF-BP from cDNA or genomic DNA banks. Such nucleic acid sequences can then be sequenced according to known methods [42]. On the basis of the thus-determined sequences and of the already known sequences for certain receptors, those partial sequences which code for soluble TNF-BP fragments can be determined and cut out from the complete sequence using known methods [42].

The complete sequence or such partial sequences can then be integrated using known methods into vectors described in the state of the art for their multiplication and expression in prokaryotes [42]. Suitable prokaryotic host organisms are, for example, gram-negative and gram-positive bacteria such as, for example, E. coli strains such as E. coli HB 101 [ATCC No. 33 694] or E. coli W3110 [ATCC No. 27 325] or B. subtilis strains.

Furthermore, nucleic acid sequences in accordance with the invention which code for TNF-BP as well as for TNF-BP fragments can be integrated using known methods into suitable vectors for reproduction and expression in eukaryotic host cells, such as, for example, yeast, insect cells and mammalian cells. Expression of such sequences is preferably effected in mammalian and insect cells.

A typical expression vector for mammalian cells contains an efficient promoter element in order to produce a good transcription rate, the DNA sequence to be expressed and signals for an efficient termination and polyadenylation of the transcript. Additional elements which can be used are "enhancers" which lead to again intensified transcription and sequences which e.g. can bring about a longer half life of the mRNA. For the expression of nucleic acid sequences in which the endogenous sequence fragment coding for a signal peptide is missing, there can be used vectors which contain such suitable sequences which code for signal peptides of other known proteins. See, for example, the vector pLJ268 described by Cullen, B. R. in Cell 46, 973–982 (1986) as well as Sharma, S. et al. in "Current Communications in Molecular Biology", edt. by Gething, M. J., Cold Spring Harbor Lab. (1985), pages 73–78.

Most of these vectors which are used for a transient expression of a particular DNA sequence in mammalian cells contain the replication source of the SV40 virus. In cells which express the T-antigen of the virus (e.g. COS cells), these vectors are reproduced abundantly. A transient expression is, however, not limited to COS cells. In principle any transfectable mammalian cell line can be used for this purpose. Signals which can bring about a strong transcription are e.g. the early and late promoters of SV40, the promoter and enhancer of the "major immediate-early" gene of HCMV (human cytomegalovirus), the LTR's ("long terminal repeats") of retroviruses such as, for example, RSV, HIV and MMTV. There can, however, also be used signals of cellular genes such as e.g. the promoters of the actin and collagenase genes.

Alternatively, however, stable cell lines which have the specific DNA sequence integrated into the genome (chromosome) can also be obtained. For this, the DNA sequence is cotransfected together with a selectable marker, e.g. neomycin, hygromycin, dihydrofolate reductase (dhfr) or hypoxanthin guanine phosphoribosyl transferase (hgpt). The DNA sequence stably incorporated in the chromosome can also be reproduced abundantly. A suitable selection marker for this is, for example, dihydrofolate reductase (dhfr). Mammalian cells (e.g. CHO cells), which contain no intact dhfr gene, are thereby incubated with increasing amounts of methotrexate after transinfection has been effected. In this manner cell lines which contain more than a thousand copies of the desired DNA sequence can be obtained.

Mammalian cells which can be used for the expression are e.g. cells of the human cell lines Hela [ATCC CCL2] and 293 [ATCC CRL 1573] as well as 3T3 [ATCC CCL 163] and L cells, e.g. [ATCC CCL 149], (CHO) cells [ATCC CCL 61], BHK [ATCC CCL 10] cells as well as the CV 1 [ATCC CCL 70] and the COS cell lines [ATCC CRL 1650, CRL 1651].

Suitable expression vectors include, for example, vectors such as pBC12MI [ATCC 67 109], pSV2dhfr [ATCC 37 146], pSVL [Pharmacia, Uppsala, Sweden], pRSVcat [ATCC 37 152] and PMSG [Pharmacia, Uppsala, Sweden]. The vectors "pK19" and "pN123" used in Example 9 are especially preferred vectors. These can be isolated according to known methods from E. coli strains HB101(pK19) and HB101(pN123) transformed with them [42]. These E. coli strains have been deposited on the 26th Jan. 1990 at the Deutschen Sammlung von Mikroorganismen und Zellkulturen GmbH (DSM) in Braunschweig, FRG, under DSM 5761 for HB101(pK19) and DMS 5764 for HB101(pN123). For the expression of proteins which consist of a soluble. fragment of non-soluble TNF-BP and an immunoglobulin fragment, i.e. all domains except the first of the constant region of the heavy chain, there are especially suitable pSV2-derived vectors as described, for example, by German, C. in "DNA Cloning" [Vol. II.,. edt. by Glover, D. M., IRL Press, Oxford, 1985]. The vectors pCD4-Hµ (DSM 5315), pDC4-Hγ1 (DSM 5314) and pCD4-Hγ3 (DSM 5523) which have been deposited at the Deutschen Sammlung von Mikroorganismen und Zellkulturen GmbH (DSM) in Braunschweig, FRG, and which are described in detail in European Patent Application No. 90107393.2 are especially preferred vectors. This European Patent Specification and the equivalent Applications referred to in Example 11 also contain data with respect to the further use of these vectors for the expression of chimeric proteins (see also Example 11) and for the construction of vectors for the expression of such chimeric proteins with other immunoglobulin fragments.

The manner in which these cells are transfected depends on the chosen expression system and vector system. An overview of these methods is to be found e.g. in Pollard et al., "DNA Transformation of Mammalian Cells" in "Methods in Molecular Biology" [Nucleic Acids Vol. 2, 1984, Walker, J. M., ed, Humana, Clifton, N.J.]. Further methods are to be found in Chen and Okayama ["High-Efficiency Transformation of Mammalian Cells by Plasmid DNA", Molecular and Cell Biology 7, 2745–2752, 1987] and in Felgner [Felgner et al., "Lipofectin: A highly efficient, lipid-mediated DNA-transfection procedure", Proc. Nat. Acad. Sci. U.S.A. 84, 7413–7417, 1987].

The baculovirus expression system, which has already been used successfully for the expression of a series of proteins (for an overview see Luckow and Summers, Bio/Technology 6, 47–55, 1988), can be used for the expression in insect cells. Recombinant proteins can be produced in authentic form or as fusion proteins. The thus-produced proteins can also be modified such as, for example, glycosylated (Smith et al., Proc. Nat. Acad. Sci. U.S.A. 82, 8404–8408, 1987). For the production of a recombinant baculovirus which expresses the desired protein there is used a so-called "transfer vector". Under this there is to be understood a plasmid which contains the heterologous DNA sequence under the control of a strong promoter, e.g. that of the polyhedron gene, whereby this is surrounded on both sides by viral sequences. The vectors "pN113", "pN119" and "pN124" used in Example 10 are especially preferred vectors. These can be isolated according to known methods from *E. coli* strains HB101(pN113), HB101(pN119) and HB101(pN124) transformed with them. These *E. coli* strains have been deposited on the 26th Jan. 1990 at the Deutschen Sammlung von Mikroorganismen und Zellkulturen GmbH (DSM) in Braunschweig, FRG, under DSM 5762 for HB101 (pN113), DSM 5763 for HB101(pN119) and DSM 5765 for HB101(pN124). The transfer vector is then transfected into the insect cells together with DNA of the wild type baculovirus. The recombinant viruses which result in the cells by homologous recombination can then be identified and isolated according to known methods. An overview of the baculovirus expression system and the methods used therein is to be found in Luckow and Summers [52].

Expressed TNF-BP as well as its non-soluble or soluble fractions can then be purified from the cell mass or the culture supernatants according to methods of protein chemistry which are known in the state of the art, such as, for example, the procedure already described on pages 5–6.

The TNF-BP obtained in accordance with the invention can also be used as antigens to produce polyclonal and monoclonal antibodies according to known techniques [44, 45] or according to the procedure described in Example 3. Such antibodies, especially monoclonal antibodies against the 75 kD TNF-BP species, are also an object of the present invention. Those antibodies which are directed against the 75 kD TNF-BP can be used for the isolation of TNF-BP by modifications of the purification procedure described in detail in Examples 4–6 which are familiar to a person skilled in the art.

On the basis of the high binding affinity of TNF-BP in accordance with the invention for TNF ($K_d$ value in the order of $10^{-9}$–$10^{-10}$M), these or fragments thereof can be used as diagnostics for the detection of TNF in serum or other body fluids according to methods known in the state of the art, for example in solid phase binding tests or in combination with anti-TNF-BP antibodies in so-called "sandwich" tests.

Moreover, TNF-BP in accordance with the invention can be used on the one hand for the purification of TNF and on the other hand for the detection of TNF agonists and TNF antagonists according to procedures which are known in the state of the art.

The TNF-BP in accordance with the invention as well as their physiologically compatible salts, which can be manufactured according to methods which are known in the state of the art, can also be used for the production of pharmaceutical preparations, primarily those for the treatment of illnesses in which TNF is involved in their course. For this purpose, one or more of the said compounds, where desired or required in combination with other pharmaceutically active substances, can be processed in a known manner with the usually used solid or liquid carrier materials. The dosage of such preparations can be effected having regard to the usual criteria in analogy to already used preparations of similar activity and structure.

Since the invention has been described hereinbefore in general terms, the following Examples are intended to illustrate details of the invention, but they are not intended to limit its scope in any manner.

EXAMPLE 1

Detection of TNF-binding Proteins

The TNF-BP were detected in a filter test with human radioiodinated $^{125}$I-TNF. TNF (46, 47) was radioactively labelled with Na$^{125}$ I (IMS40, Amersham, Amersham, England) and iodo gene (#28600, Pierce Eurochemie, Oud-Beijerland, Netherlands) according to Fraker and Speck [48]. For the detection of the TNF-BP, isolated membranes of the cells or their solubilized, enriched and purified fractions were applied to moist nitrocellulose filter (0.45 μ, BioRad, Richmond, Calif., U.S.A.). The filters were then blocked in buffer solution with 1% skimmed milk powder and subsequently incubated with $5·10^5$ cpm/ml of $^{125}$I-TNFα (0.3–$1.0·10^8$ cpm/μg) in two batches with and without the addition of 5 μg/ml of non-labelled TNFα, washed and dried in the air. The bound radioactivity was detected semiquantitatively by autoradiography or counted in a gamma-counter. The specific $^{125}$I-TNF-α binding was determined after correction for unspecific binding in the presence of unlabelled TNF-α in excess. The specific TNF-binding in the filter test was measured at various TNF concentrations and analyzed according to Scatchard, whereby a $K_d$ value of $10^{-9}$–$10^{-10}$M was determined.

EXAMPLE 2

Cell extracts of HL-60 cells

HL60 cells [ATCC No. CCL 240] were cultivated on an experimental laboratory scale in a RPMI 1640 medium [GIBCO catalogue No. 074-01800], which contained 2 g/l NaHCO$_3$ and 5% foetal calf serum, in a 5% CO$_2$ atmosphere and subsequently centrifuged.

The following procedure was used to produce high cell densities on an industrial scale. The cultivation was carried out in a 75 l Airlift fermenter (Fa. Chemap, Switzerland)

with a working volume of 58 l. For this there was used the cassette membrane system "PROSTAK" (Millipore, Switzerland) with a membrane surface of 0.32 m² (1 cassette) integrated into the external circulation circuit. The culture medium (see Table 1) was pumped around with a Watson-Marlow pump, Type 603U, with 5 l/min. After a steam sterilization of the installation, whereby the "PROSTAK" system was sterilized separately in autoclaves, the fermentation was started with growing HL-60 cells from a 20 l Airlift fermenter (Chemap). The cell cultivation in the inoculation fermenter was effected in a conventional batch process in the medium according to Table 1 and an initial cell titre of $2 \times 10^5$ cells/ml. After 4 days the HL60 batch was transferred with a titre of $4.9 \times 10^6$ cells/ml into the 75 l fermenter. The pH value was held at 7.1 and the $pO_2$ value was held at 25% saturation, whereby the oxygen introduction was effected through a microporous frit. After initial batch fermentation, on the 2nd day the perfusion at a cell titre of $4 \times 10^6$ cells/ml was started with 30 l of medium exchange per day. On the filtrate side of the medium the conditioned medium was removed and replaced by the addition of fresh medium. The added medium was fortified as follows: Primatone from 0.25% to 0.35%, glutamine from 5 mM to 6 mM and glucose from 4 g/l to 6 g/l. The perfusion rate was then increased on the 3rd and 4th day to 72 l of medium/day and on the 5th day to 100 l of medium/day. The fermentation had finished after 120 hours of continuous cultivation. Exponential cell growth up to $40 \times 10^6$ cells/ml took place under the given fermentation conditions. The duplication time of the cell population was 20–22 hours to $10 \times 10^6$ cells/ml and then increased to 30–36 hours with increasing cell density. The proportion of living cells lay at 90–95% during the entire fermentation period. The HL-60 batch was then cooled down in the fermenter to about 12° C. and the cells were harvested by centrifugation (Beckman centrifuge [Model J-6B, Rotor JS], 3000 rpm, 10 min., 4° C).

TABLE 1

| HL-60 medium Components | Concentrations mg/l |
|---|---|
| CaCl$_2$ (anhydrous) | 112.644 |
| Ca(NO$_3$)$_2$.4H$_2$O | 20 |
| CuSO$_4$.5H$_2$O | $0.498 \cdot 10^{-3}$ |
| Fe(NO$_3$)$_3$.9H$_2$O | 0.02 |
| FeSO$_4$.7H$_2$O | 0.1668 |
| KCl | 336.72 |
| KNO$_3$ | 0.0309 |
| MgCl$_2$ (anhydrous) | 11.444 |
| MgSO$_4$ (anhydrous) | 68.37 |
| NaCl | 5801.8 |
| Na$_2$HPO$_4$ (anhydrous) | 188.408 |
| NaH$_2$PO$_4$.H$_2$O | 75 |
| Na$_2$SeO$_3$.5H$_2$O | $9.6 \cdot 10^{-3}$ |
| ZnSO$_4$.7H$_2$O | 0.1726 |
| D-Glucose | 4000 |
| Glutathion (red.) | 0.2 |
| Hepes buffer | 2383.2 |
| Hypoxanthin | 0.954 |
| Linoleic acid | 0.0168 |
| Lipoic acid | 0.042 |
| Phenol Red | 10.24 |
| Putrescine 2HCl | 0.0322 |
| Na pyruvate | 88 |
| Thymidine | 0.146 |
| Biotin | 0.04666 |
| D-Ca pantothenate | 2.546 |
| Choline chloride | 5.792 |
| Folic acid | 2.86 |
| i-Inositol | 11.32 |
| Niacinamide | 2.6 |

TABLE 1-continued

| HL-60 medium Components | Concentrations mg/l |
|---|---|
| Nicotinamide | 0.0074 |
| para-Aminobenzoic acid | 0.2 |
| Pyridoxal HCl | 2.4124 |
| Pyridoxin HCl | 0.2 |
| Riboflavin | 0.2876 |
| Thiamin HCl | 2.668 |
| Vitamin B$_{12}$ | 0.2782 |
| L-Alanine | 11.78 |
| L-Aspartic acid | 10 |
| L-Asparagine H$_2$O | 14.362 |
| L-Arginine | 40 |
| L-Arginine HCl | 92.6 |
| L-Aspartate | 33.32 |
| L-Cystine 2HCl | 62.04 |
| L-Cysteine HCl.H$_2$O | 7.024 |
| L-Glutamic acid | 36.94 |
| L-Glutamine | 730 |
| L-Glycine | 21.5 |
| L-Histidine | 3 |
| L-Histidine HCl.H$_2$O | 27.392 |
| L-Hydroxypyroline | 4 |
| L-Isoleucine | 73.788 |
| L-Leucine | 75.62 |
| L-Lysine HCl | 102.9 |
| L-Methionine | 21.896 |
| L-Phenylalanine | 43.592 |
| L-Proline | 26.9 |
| L-Serine | 31.3 |
| L-Threonine | 53 |
| L-Tryptophan | 11.008 |
| L-Tyrosine.2Na | 69.76 |
| L-Valine | 62.74 |
| Penicillin/streptomycin | 100 U/ml |
| Insulin (human) | 5 μg/ml |
| Tranferrin (human) | 15 μg/ml |
| Bovine serum albumin | 67 μg/ml |
| Primatone RL (Sheffield Products, Norwich NY, USA) | 0.25% |
| Pluronic F68 (Serva, Heidelberg, FRG) | 0.01% |
| Foetal calf serum | 0.3–3% |

The centrifugate was washed with isotonic phosphate buffer (PBS; 0.2 g/l KCl, 0.2 g/l KH$_2$PO$_4$, 8.0 g/l NaCl, 2.16 g/l Na$_2$HPO$_4$·7H$_2$O), which had been treated with 5% dimethylformamide, 10 mM benzamidine, 100 μ/ml aprotinin, 10 μM leupeptin, 1 μM pepstatin, 1 mM o-phenanthroline, 5 mM iodoacetamide, 1 mM phenylmethylsulphonyl fluoride (referred to hereinafter as PBS-M). The washed cells were extracted at a density of $2.5 \cdot 10^8$ cells/ml in PBS-M with Triton X-100 (final concentration 1.0%). The cell extract was clarified by centrifugation (15,000×g, 1 hour; 100,000×g, 1 hour).

EXAMPLE 3

Production of monoclonal (TNF-BP) antibodies

A centrifugation supernatant from the cultivation of HL60 cells on an experimental laboratory scale, obtained according to Example 2, was diluted with PBS in the ratio 1:10. The diluted supernatant was applied at 4° C. (flow rate 0.2 ml/min.) to a column which contained 2 ml of Affigel 10 (Bio Rad Catalogue No. 153-6099) to which had been coupled 20 mg of recombinant human TNF-α [Pennica, D. et al. (1984) Nature 312, 724; Shirai, T. et al. (1985) Nature 313, 803; Wang, A. M. et al. (1985) Science 228, 149] according to the recommendations of the manufacturer. The column was washed at 4° C. and a throughflow rate of 1 ml/min firstly with 20 ml of PBS which contained 0.1% Triton X 114 and thereafter with 20 ml of PBS. Thus-enriched TNF-BP was eluted at 22° C. and a flow rate of 2 ml/min with 4 ml of 100 mM glycine, pH 2.8, 0.1% decylmaltoside. The eluate was concentrated to 10 μl in a Centricon 30 unit [Amicon].

10 μl of this eluate were mixed with 20 μl of complete Freund's adjuvant to give an emulsion. 10 μl of the emulsion were injected according to the procedure described by Holmdahl, R. et al. [(1985), J. Immunol. Methods 83, 379] on each of days 0, 7 and 12 into a hind paw of a narcotized Balb/c mouse.

The immunized mice were sacrificed on day 14, the popliteal lymph nodes were removed, minced and suspended by repeated pipetting in Iscove's medium (IMEM, GIBCO Catalogue No. 074-2200) which contained 2 g/l $NaHCO_3$. According to a modified procedure of De St. Groth and Scheidegger [J. Immunol. Methods (1980), 35, 1] $5 \times 10^7$ cells of the lymph nodes were fused with $5 \times 10^7$ PAI mouse myeloma cells (J. W. Stocker et al., Research Disclosure, 217, May 1982, 155–157) which were in logarithmic growth. The cells were mixed, collected by centrifugation and resuspended in 2 ml of 50% (v/v) polyethylene glycol in IMEM at room temperature by slight shaking and diluted by the slow addition of 10 ml of IMEM during careful shaking for 10 minutes. The cells were collected by centrifugation and resuspended in 200 ml of complete medium [IMEM+20% foetal calf serum, glutamine (2.0 mM), 2-mercaptoethanol (100 μM), 100 μM hypoxanthine, 0.4 μM aminopterine and 16 μM thymidine (HAT)]. The suspension was distributed on 10 tissue culture dishes each containing 96 wells and incubated at 37° C. for 11 days without changing the medium in an atmosphere of 5% $CO_2$ and a relative humidity of 98%.

The antibodies are distinguished by their inhibitory action on the binding of TNF to HL60 cells or by their binding to antigens in the filter test according to Example 1. The following procedure was used to detect the biological activity of anti(TNF-BP) antibodies: $5 \times 10^6$ HL60 or U937 cells were incubated in complete RPMI 1640 medium together with affinity-purified monoclonal anti-(TNF-BP) antibodies or control antibodies (i.e. those which are not directed against TNF-BP) in a concentration range of 1 ng/ml to 10 μg/ml. After incubation at 37° C. for one hour the cells were collected by centrifugation and washed with 4.5 ml of PBS at 0° C. They were resuspended in 1 ml of complete RPMI 1640 medium (Example 2) which additionally contained 0.1% sodium azide and $^{125}$I-TNFα ($10^6$ cpm/ml) with or without the addition of unlabelled TNFα (see above). The specific radioactivity of the $^{125}$I-TNFα amounted to 700 Ci/mmol. The cells were incubated at 4° C. for 2 hours, collected and washed 4 times at 0° C. with 4.5 ml of PBS which contained 1% BSA and 0.001% Triton X 100 (Fluka). The radioactivity bound to the cells was measured in a γ-scintillation counter. The cell-bound radioactivity of cells which had not been treated with anti-(TNF-BP) antibodies was determined in a comparative experiment (approximately 10 000 cpm/$5 \times 10^6$ cells).

EXAMPLE 4
Affinity chromatography

For the further purification, a monoclonal anti-(55 kD TNF-BP) antibody (2.8 mg/ml gel), obtained according to Example 3, TNFα (3.9 mg/ml gel) and bovine serum albumin (BSA, 8.5 mg/ml gel) were each covalently coupled to CNBr-activated Sepharose 4B (Pharmacia, Uppsala, Sweden) according to the directions of the manufacturer. The cell extract obtained according to Example 2 was passed through the thus-prepared columns which were connected in series in the following sequence: BSA-Sepharose precolumn, immune affinity column [anti-(55 kD-TNF-BP) antibody], TNFα-ligand affinity column. After completion of the application the two last-mentioned columns were separated and washed individually with in each case 100 ml of the following buffer solutions: (1) PBS, 1,0% Triton X-100, 10 mM benzamidine, 100 U/ml aprotinin; (2) PBS, 0.1% Triton X-100, 0.5M NaCl, 10 mM ATP, 10 mM benzamidine, 100 U/ml aprotinin; and (3) PBS, 0.1% Triton X-100, 10 mM benzamidine, 100 U/ml aprotinin. Not only the immune affinity column, but also the TNFα-ligand affinity column were then each eluted with 100 mM glycine pH 2.5, 100 mM NaCl, 0.2% decylmaltoside, 10 mM benzamidine, 100 U/ml aprotinin. The fractions of each column which were active in the filter test according to Example 1 were thereafter combined and neutralized with 1M Tris pH 8.0.

The thus-combined TNF-BP active fractions of the immune affinity chromatography on the one hand and of the TNFα-ligand affinity chromatography on the other hand were, for further purification, again applied to in each case one small TNFα-ligand affinity column. Thereafter, these two columns were washed with in each case 40 ml of (1) PBS, 1.0% Triton X-100, 10 mM benzamidine, 100 U/ml aprotinin, (2) PBS, 0.1% Triton X-100, 0.5M NaCl, 10 mM ATP, 10 mM benzamidine, 100 U/ml aprotinin, (3) PBS, 0.1% Triton X-100, (4) 50 mM Tris pH 7.5, 150 mM NaCl, 1.0% NP-40, 1.0% desoxycholate, 0.1% SDS, (5) PBS, 0.2% decylmaltoside. Subsequently, the columns were eluted with 100 mM glycine pH 2.5, 100 mM NaCl, 0.2% decylmaltoside. Fractions of 0.5 ml from each column were collected and the fractions from each column which were active according to the filter test (Example 1) were combined and concentrated in a Centricon unit (Amicon, molecular weight exclusion 10,000).

EXAMPLE 5
Separation by means of HPLC

The active fractions obtained according to Example 4 were each applied according to their different source (immune or ligand affinity chromatography) to C1/C8 reversed phase HPLC columns (ProRPC, Pharmacia, 5×20 mm) which had been equilibrated with 0.1% trifluoroacetic acid, 0.1% octylglucoside. The columns were then eluted with a linear acetonitrile gradient (0–80%) in the same buffer at a flow of 0.5 ml/min. Fractions of 1.0 ml were collected from each column and the active fractions from each column were combined (detection according to Example 1).

EXAMPLE 6
Separation by means of SDS-PAGE

The fractions which were obtained according to Example 5 and which were active according to the filter test (Example 1) were further separated by SDS-PAGE according to [34]. For this purpose, the samples were heated to 95° C. for 3 minutes in SDS sample buffer and subsequently separated electrophoretically on a 12% acrylamide separation gel with a 5% collection gel. The following standard proteins were used as a reference for the determination of the apparent molecular weights on the SDS-PAGE gel: phosphorylase B (97.4 kD), BSA (66.2 kD), ovalbumin (42.7 kD), carboanhydrase (31.0 kD), soya trypsin inhibitor (21.5 kD) and lysozyme (14.4 kD).

Under the mentioned conditions there were obtained for samples which has been obtained according to Example 4 by TNF-α-ligand affinity chromatography of immune affinity chromatography eluates and which had been further separated by HPLC according to Example 5 two bands of 55 kD and 51 kD as well as three weaker bands of 38 kD, 36 kD and 34 kD. These bands were transferred electrophoretically during 1 hour at 100 V in 25 mM Tris, 192 mM glycine, 20% methanol on to a PVDF membrane (Immobilon, Millipore, Bedford, Mass. U.S.A.) in a Mini Trans Blot System (BioRad, Richmond, Calif., U.S.A.). Thereafter, the PVDF membrane was either protein-stained with 0.15% Serva-Blue (Serva, Heidelberg, FRG) in methanol/water/glacial acetic acid (50/40/10 parts by volume) or blocked with skimmed milk powder and subsequently incubated with $^{125}$I-TNFα according to the filter test conditions described in Example 1 in order to detect bands having TNF-BP activity. This showed that all bands produced in the protein staining bonded TNFα specifically. In the Western blot according to Towbin et al. [38] all of these bands also bonded the monoclonal anti-55 kD-TNF-BP antibody produced according to Example 3. In this case, a procedure according to that described in Example 1 with Na$^{125}$I radioactively-labelled, affinity-purified (mouse immunoglobulin-Sepharose-4B affinity column) rabbit-anti-mouse-immunoglobulin antibody was used for the autoradiographic detection of this antibody.

Samples which had been obtained according to Example 4 by two-fold TNF-α-ligand affinity chromatography of the throughput of the immune affinity chromatography and which had been further separated by HPLC according to Example 5 showed under the above-specified SDS-PAGE and blot transfer conditions two additional bands of 75 kD and 65 kD, both of which bonded TNF specifically in the filter test (Example 1). In the Western blot according to Towbin et al. (see above) the proteins of these two bands did not react with the anti-(55 kD TNF-BP) antibody produced according to Example 3. They reacted, however, with a monoclonal antibody which had been produced starting from the 75 kD band (anti-75 kD TNF-BP antibody) according to Example 3.

EXAMPLE 7

Amino acid sequence analysis

For the amino acid sequence analysis, the fractions which had been obtained according to Example 5 and which were active according to the filter test (Example 1) were separated using the SDS-PAGE conditions described in Example 6, but now reducing (SDS sample buffer with 125 mM dithiothreitol). The same bands as in Example 6 were found, but because of the reducing conditions of the SDS-PAGE in comparison to Example 6 all showed an about 1–2 kD higher molecular weight. These bands were then transferred according to Example 6 on to PVDF membranes and stained with 0.15% Serva-Blue in methanol/water/ glacial acetic acid (50/400/10 parts by volume) for 1 minute, decolorized with methanol/water/glacial acetic acid (45/48/7 parts by volume), rinsed with water, dried in air and thereafter cut out. The conditions given by Hunkapiller [34] were adhered to in all steps in order to avoid N-terminal blocking. Initially, the purified TNF-BP were used unaltered for the amino acid sequencing. In order to obtain additional sequence information, the TNF-BP after reduction and S-carboxymethylation [Jones, B. N. (1986) in "Methods of Protein Micro-characterisation", J. E. Shively, ed., Humana Press, Clifton N.J., 124–125] were cleaved with cyanogen bromide (Tarr, G. E. in "Methods of Protein Microcharacterisation", 165–166, loc. cit.), trypsin and/or proteinase K and the peptides were separated by HPLC according to known methods of protein chemistry. Thus-prepared samples were then sequenced in an automatic gas phase microsequencing apparatus (Applied Biosystems Model 470A, ABI, Foster City, Calif., U.S.A.) with an on-line automatic HPLC PTH amino acid analyzer (Applied Biosystems Model 120, ABI see above) connected to the outlet, whereby the following amino acid sequences were determined:

1., For the 55 kD band (according to non-reducing SDS-PAGE):
  Leu-Val-Pro-His-Leu-Gly-Asp-Arg-Glu-Lys-Arg-Asp-Ser-Val-Cys-Pro-Gln-Gly-Lys-Tyr-Ile-His-Pro-Gln-X-Asn-Ser-Ile, and
  Ser-Thr-Pro-Glu-Lys-Glu-Gly-Glu-Leu-Glu-Gly-Thr-Thr-Thr-Lys in which X stands for an amino acid residue which could not be determined, 2., for the 51 kD and 38 kD bands (according to non-reducing SDS-PAGE):
  Leu-Val-Pro-His-Leu-Gly-Asp-Arg-Glu 3., for the 65 kD band (according to non-reducing SDS-PAGE:

In the N-terminal sequencing of the 65 kD band two parallel sequences were determined up to the 15th residue without interruption. Since one of the two sequences corresponded to a partial sequence of ubiquitin [36, 37], the following sequence was derived for the 65 kD band:
  Leu-Pro-Ala-Gln-Val-Ala-Phe-X-Pro-Tyr-Ala-Pro-Glu-Pro-Gly-Ser-Thr-Cys.

in which X stands for an amino acid residue which could not be determined.

Additional peptide sequences for 75(65) kDa-TNF-BP were determined:

Ile-X-Pro-Gly-Phe-Gly-Val-Ala-Tyr-Pro-Ala-Leu-Glu and

Ser-Gln-Leu-Glu-Thr-Pro-Glu-Thr-Leu-Leu-Gly-Ser-Thr-Glu-Glu-Lys-Pro-Leu and

Val-Phe-Cys-Thr and

Asn-Gln-Pro-Gln-Ala-Pro-Gly-Val-Glu-Ala-Ser-Gly-Ala-Gly-Glu-Ala and

Leu-Cys-Ala-Pro and

Val-Pro-His-Leu-Pro-Ala-Asp and

Gly-Ser-Gln-Gly-Pro-Glu-Gln-Gln-X-X-Leu-Ile-X-Ala-Pro, in which X stands for an amino acid residue which could not be determined.

Example 8

Determination of base sequences of complementary DNA (cDNA)

Starting from the amino acid sequence according to formula IA there were synthesized having regard to the genetic code for the amino acid residues 2–7 and 17–23 corresponding completely degenerated oligonucleotides in suitable complementarity ("sense" and "antisense" oligonucleotides). Total cellular RNA was isolated from HL60 cells [42, 43] and the first cDNA strand was synthesized by oligo-dT priming or by priming with the "antisense" oligonucleotide using a cDNA synthesis kit (RPN 1256, Amersham, Amersham, England) according to the instructions of the manufacturer. This cDNA strand and the two synthesized degenerate "sense" and "anti-sense" oligonucleotides were used in a polymerase chain reaction (PCR, Perkin Elmer Cetus, Norwalk, Conn., U.S.A. according to the instructions of the manufacturer) to synthesize as a cDNA fragment the base sequence coding for the amino acid residues 8–16 (formula IA). The base sequence of this cDNA fragment accorded to: 5'-AGGGAGAAGAGAGATAGTGTGTGTCCC-3'. This cDNA fragment was used as a probe in order to identify according to a known procedure a cDNA clone coding for the 55 kD TNF-BP in a λgt11-cDNA gene bank from human placenta (42, 43). This clone was then cut according to usual methods from the λ-vector and cloned in the plasmids pUC18 (Pharmacia, Uppsala, Sweden) and pUC19 (Pharmacia, Uppsala, Sweden) and in the M13mp18/M13mp19 bacteriophage (Pharmacia, Uppsala, Sweden) (42, 43). The nucleotide sequence of this cDNA clone was determined using a Sequenase kit (U.S. Biochemical, Cleveland, Ohio., U.S.A.) according to the details of the manufacturer. The nucleotide sequence and the amino acid sequence derived therefrom for the 55 kD TNF-BP and its signal peptide (amino acid "−28" to amino acid "0") is given in FIG. 1 using the abbreviations for bases such as amino acids usual in the state of the art. From sequence comparisons with other already known receptor protein sequences there can be determined a N-terminal domain containing approximately 180 amino acids and a C-terminal domain containing 220 amino acids which are separated from one another by a transmembrane region of 19 amino acids (underlined in FIG. 1) which is typical according to the sequence comparisons. Hypothetical glycosylation sites are characterized in FIG. 1 by asterisks above the corresponding amino acid.

Essentially analogous techniques were used to identify 75/65 kD TNF-BP-coding partial cDNA sequences, whereby, however, in this case genomic human DNA and completely degenerated 14-mer and 15-mer "sense" and "antisense" oligonucleotides derived from peptide IIA were used in order to produce a primary 26 bp cDNA probe in a polymerase chain reaction. This cDNA probe was then used in a HL-60 cDNA library to identify cDNA clones of different lengths. This cDNA library was produced using isolated HL60 RNA and a cDNA cloning kit (Amersham) according to the details of the manufacturer. The sequence of such a cDNA clone is given in FIG. 4, whereby repeated sequencing lead to the following correction. A threonine coded by "ACC" not "TCC", has to be at position 3 instead of the serine.

EXAMPLE 9
Expression in COS 1 cells

Vectors starting from the plasmid "pN11" were constructed for the expression in COS cells. The plasmid "pN11" contains the efficient promotor and enhancer of the "major immediate-early" gene of human cytomegalovirus ("HCMV"; Boshart et al., Cell 41, 521–530, 1985). After the promotor there is situated a short DNA sequence which contains several restriction cleavage sites, which are present only once in the plasmid ("polylinker"), inter alia the cleavage sites for HindIII, BalI, BamHI and PvuII (see sequence).

PvuII

5'-AAGCTTGGCCAGGATCCAGCTGACTGACTGAT
CGCGAGATC-3'
3'-TTCGAACCGGTCCTAGGTCGACTGACTGACTA
GCGCTCTAG-5'

After these cleavage sites there are situated three translation stop codons in all three reading frames. After the polylinker sequence there is situated the 2nd intron and the polyadenylation signal of the preproinsulin gene of the rat (Lomedico et al., Cell 18, 545–558, 1979). The plasmid also contains the replication origin of the SV40 virus and a fragment from pBR322 which confers E. coli-bacteria ampicillin resistance and permits the replication of the plasmid in E. coli.

For the construction of the expression vector "pN123", this plasmid "pN11" was cleaved the restriction endonuclease PvuII and subsequently treated with alkaline phosphatase. The dephosphorylated vector was thereafter isolated from an agarose gel (V1). The 5'-projecting nucleotides of the EcoRI-cleaved 1.3 kb fragment of the 55 kD TNF-BP-cDNA (see Example 8) were filled in using Klenow enzyme. Subsequently, this fragment was isolated from an agarose gel (F1). Thereafter, V1 and F1 were joined together using T4-ligase. E. coli HB101 cells were then transformed with this ligation batch according to known methods [42]. By means of restriction analyses and DNA sequencing according to known methods [42] there were identified transformants which had been transformed with a plasmid and which contained the 1.3 kb EcoRI fragment of the 55 kD TNF-BP-cDNA in the correct orientation for expression via the HCMV-promoter. This vector received the designation "pN123".

The following procedure was used for the construction of the vector "pK19". A DNA fragment which contained only the cDNA coding for the extracellular part of the 55 kD TNF-BP (amino acids −28 to 182 according to FIG. 1) was obtained by PCR technology (Saiki et al., Science 230, 1350–1354, 1985, see also Example 8). The following oligonucleotides were used in order to amplify the cDNA from "pN123" coding for the extracellular part of the 55 kD TNF-BP:

BAMHI

5'-CACAGGGATCCATAGCTGTCTGGCATGGGCCT
CTCCAC-3'

ASP718

3'-CGTGACTCCTGAGTCCGTGGTGTATTATCTCTA
GACCATGGCCC-5'

By means of these oligonucleotides there were also introduced two stop codons of the translation after amino acid 182. The thus-amplified DNA fragment was cleaved with then ligated with V1 and the entire batch was used for the transformation of E. coli HB101, as already described.

Transformants which had been transformed with a plasmid containing the DNA fragment in the correct orientation for the expression via the HCMV-promoter were identified by DNA sequencing (see above). The plasmid isolated therefrom received the designation "pK19".

Figure 2B:
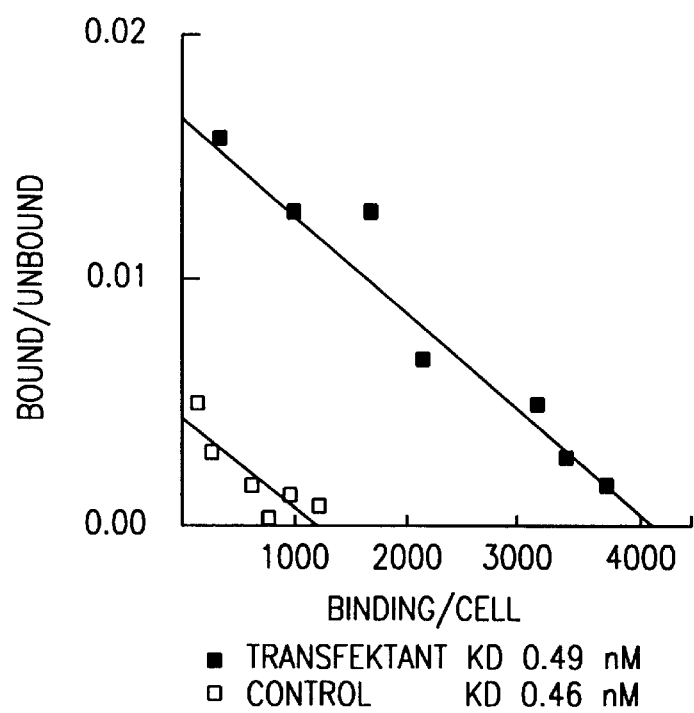
Figure 3:
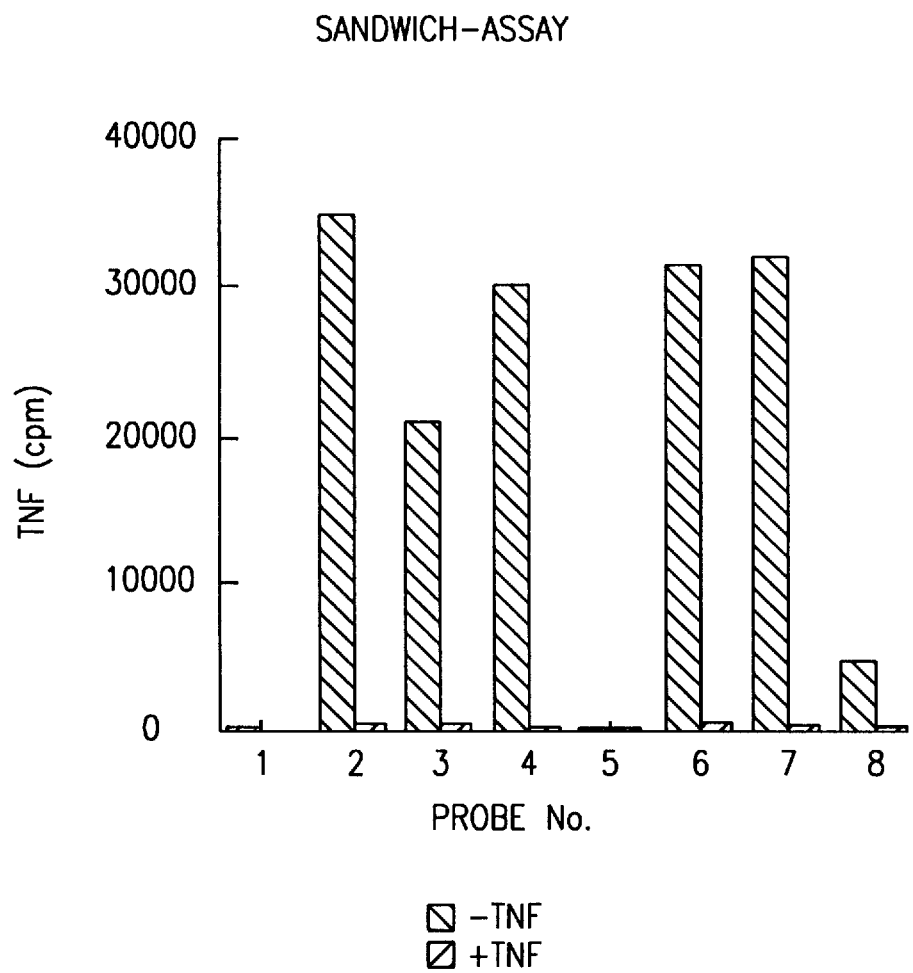
FIG. 3. Sandwich assays of cells transfected with plasmid pK19. Culture supernatants of cells transfected with pK19 were incubated with anti-55 kD TNF-BP antibody followed by $^{125}$I-TNFα. Columns 1, 5, and 8 are controls. Columns 2, 3, 4, 5, and 6 are five parallel transfections.

Transfection of the COS cells with the plasmids "pN123" or "pK19" was carried out according to the lipofection method published by Felgner et al. (Proc. Natl. Acad. Sci. U.S.A. 84, 7413–7417, 1987). 72 hours after the transfection had been effected the cells transfected with "pN123" were analyzed for binding with $^{125}$I-TNFα according to known methods. The results of the Scatchard analysis [Scatchard, G., Ann. New York Acad. Sci. 51, 660, 1949] of the thus-obtained binding data (FIG. 2A) is given in FIG. 2B. The culture supernatants of the cells transfected with "pK19" were investigated in a "sandwich" test. For this purpose, PVC microtitre plates (Dynatech, Arlington, Va., U.S.A.) were sensitized with 100 µl/well of a rabbit-anti-mouse immunoglobulin (10 µg/ml PBS). Subsequently, the plates were washed and incubated (3 hours, 20° C.) with an anti-55 kD TNF-BP antibody which had been detected by its antigen binding and isolated according to Example 3, but which did not inhibit the TNF-binding to cells. The plates were then again washed and incubated overnight at 4° C. with 100 µl/well of the culture supernatant (diluted 1:4 with buffer A containing 1% skimmed milk powder: 50 mM Tris/HCl pH 7.4, 140 mM NaCl, 5 mM EDTA, 0.02% Na azide). The plates were emptied and incubated at 4° C. for 2 hours with buffer A containing $^{25}$I-TNFα ($10^6$ cpm/ml, 100

μl/well) with or without the addition of 2 μg/ml of unlabelled TNF. Thereafter, the plates were washed 4 times with PBS, the individual wells were cut out and measured in a λ-counter. The results of 5 parallel transfections (columns # 2, 3, 4, 6 and 7), of two control transfections with the pN11 vector (columns # 1, 5) and of a control with HL60 cell lysate (column # 8) are given in FIG. 3.

Example 10

Expression in insect cells

The plasmid "pVL941" (Luckow and Summers, 1989, "High Level Expression of Nonfused Foreign Genes with Autographa california Nuclear Polyhedrosis virus Expression Vectors", Virology 170, 31–39) was used for the expression in a baculovirus expression system and was modified as follows. The single EcoRI restriction cleavage site in "pVL941" was removed by cleaving the plasmid with EcoRI and the projecting 5'-end was filled in with Klenow enzyme. The plasmid pVL941/E obtained therefrom was digested with BamHI and Asp718 and the vector trunk was subsequently isolated from an agarose gel. This fragment was ligated with a synthetic oligonucleotide of the following sequence:

BamHI EcoRI Asp718

5'-GATCCAGAATTCATAATAG-3'
3'-GTCTTAAGTATTATCCATG-5'

E. coli HB101 was transformed with the ligation batch and transformants containing a plasmid in which the oligonucleotide had been incorporated correctly were identified by restriction analysis and DNA sequencing according to known methods (see above); this plasmid was named "pNR704". For the construction of the transfer vector "pN113", this plasmid "pNR704" was cleaved with EcoRI, treated with alkaline phosphatase and the thus-produced vector trunk (V2) was subsequently isolated from an agarose.gel. The 1.3 kb fragment of the 55 kD TNF-BP-cDNA cleaved with EcoRI as above was ligated with fragment V2. Transformants obtained with this ligation batch, which contained a plasmid containing the cDNA insert in the correct orientation for the expression via the polyhedron promoter, were identified (see above). The vector isolated therefrom received the designation "pN113".

The following procedure was used for the construction of the transfer vector "pN119". The 1.3 kb EcoRI/EcoRI fragment of the 55 kD TNF-BP cDNA in the "pUC19" plasmid (see Example 8) was digested with BanI and ligated with the following synthetic oligonucleotide:

BanI Asp718

5'-GCACCACATAATAGAGATCTGGTACCGGGAA-3'
3'-GTGTATTATCTCTAGACCATGGCCC-5'

Two stop codons of the translation after amino acid 182 and a cleavage site for the restriction endo-nuclease Asp718 are incorporated with the above adaptor. After carrying out ligation the batch was digested with EcoRI and Asp718 and the partial 55 kD TNF-BP fragment (F3) was isolated. Furthermore, the plasmid "pNR704", likewise cleaved with Asp718 and EcoRI, was ligated with F3 and the ligation batch was transformed into E. coli HB101. The identification of the transformants which contained a plasmid in which the partial 55 kD TNF-BP cDNA had been correctly integrated for the expression was effected as already described. The plasmid isolated from these transformants received the name "pN119".

The following procedure was used for the construction of the transfer vector "pN124". The cDNk fragment coding for the extracellular part of the 55 kD TNF-BP, described in Example 9, was amplified with the specified oligonucleotides with the aid of PCR technology as described in Example 9. This fragment was cleaved with BamHI and Asp718 and isolated from an agarose gel (F4). The plasmid "pNR704" was also cleaved with BamHI and Asp718 and the vector trunk (V4) was isolated (see above). The fragments V4 and F4 were ligated, E. coli HB101 was transformed therewith and the recombinant transfer vector "pN124" was identified and isolated as described.

The following procedure was used for the transfection of the insect cells. 3 μg of the transfer vector "pN113" were transfected with 1 μg of DNA of the Autographa californica nuclear polyhedrosisvirus (AcMNPV) (EP 127839) in Sf9 cells (ATCC CRL 1711). Polyhedron-negative viruses were identified and purified from "plaques" [52]. Sf9 cells were again infected with these recombinant viruses as described in [52]. After 3 days in the culture the infected cells were investigated for TNF-binding using $^{125}$I-TNFα. For this purpose, the transfected cells were washed from the cell culture dish with a Pasteur pipette and resuspended at a cell density of 5×10$^6$ cells/ml of culture medium [52] which contained 10 ng/ml of $^{125}$I-TNF-α, not only in the presence of, but also in the absence of 5 μg/ml of non-labelled TNF-α and incubated on ice for 2 hours. Thereafter, the cells were washed with pure culture medium and the cell-bound radioactivity was counted in a γ-counter (see Table 2).

TABLE 2

| Cells | Cell-bound radioactivity per 10$^6$ cells |
|---|---|
| Non-infected cells (control) | 60 cpm |
| Infected cells | 1600 ± 330 cpm[1] |

[1]Average and standard deviation from 4 experiments

EXAMPLE 11

Analogously to the procedure described in Example 9, the cDNA fragment coding for the extracellular region of the 55 kDa TNF-BP was amplified in a polymerase chain reaction, but now using the following oligonucleotides as the primer:

Oligonucleotide 1:

Sst I

5'-TAC GAG CTC GGC CAT AGC TGT CTG GCA TG-3'

Oligonucleotide 2:

Sst I

5'-ATA GAG CTC TGT GGT GCC TGA GTC CTC AG-3'

This CDNA fragment was ligated in the pCD4-Hγ3 vector [DSM 5523; European Patent Application No. 90107393.2; Japanese Patent Application No. 108967/90; U.S. Pat. Application Ser. No. 510773/90] from which the CD4-cDNA had been removed via the SstI restriction cleavage sites. SstI cleavage sites are situated in vector pCD4-Hγ3 not only in front of, but also behind the CD4-partial sequence fragment. The construction was transfixed in J558 myeloma cells (ATCC No. TIB6) by means of protoplast fusion according to Oi et al. (Procd. Natl. Acad. Sci. U.S.A. 80, 825–829, 1983). Transfectants were selected by adding 5 μg/ml of mycophenolic acid and 250 μg/ml of xanthin (Traunecker et al., Eur. J. Immunol. 16, 851–854 [1986]) in basic medium (Dulbecco's modified Eagle's Medium, 10% foetal calf serum, 5×10$^{-5}$M 2-mercaptoethanol). The expression product secreted by the transfixed cells could be purified using usual methods of protein chemistry, e.g. TNF-BP-antibody affinity chromatography. Unless not already specifically indicated, standard procedures as described e.g. by Freshney, R. I. in "Culture of Animal Cells", Alan R. Liss, Inc., New York (1983) were used for the cultivation of the cell lines employed, for the cloning, for the selection or for the expansion of the cloned cells.

REFERENCES

1. G. E. Nedwin, S. L. Naylor, A. Y. Sakaguchi, D. Smith, J. Jarrett-Nedwin, D. Pennica, D. V. Goeddel and P. W. Gray: Nucl. Acids Res. 13, 6361, 1985
2. B. Beutler and A. Cerami: New England J. Med. 316, 379, 1987
3. L. J. Old: Science 230, 630, 1985
4. G. Trinchieri, M. Kobayashi, M. Rosen, R. Loudon, M. Murphy and B. Perussia: J. exp. Med. 164, 1206, 1986
5. J. Vilcek, V. J. Palombella, D. Henriksen-de Stefano, C. Swenson, R. Feinman, M. Hirai and M. Tsujimoto: J. exp. Med. 163, 632, 1986
6. B. J. Sugarman, B. B. Aggarwal, P. E. Hass, I. S. Figari, M. A. Palladino and H. M. Shepard: Science 230, 943, 1985
7. J. R. Gamble, J. M. Harlan, S. J. Klebanoff and M. A. Vadas: Proc. Natl. Acad. Sci. U.S.A. 82, 8667, 1985
8. N. Sato, T. Goto, K. Haranaka, N. Satomi, H. Nariuchi, Y. Mano and Y. Sawasaki: J. Natl. Cancer Inst. 76, 1113, 1986
9. A. H. Stolpen, E. C. Guinan, W. Fiers and J. S. Pober: Am. J. Pathol. 123, 16, 1986
10. J. S. Pober, L. A. Lapierre, A. H. Stolpen, T. A. Brock, T. A. Springer, W. Fiers, M. P. Bevilacqua, D. L. Mendrick and M. A. Gimbrone: J. Immunol. 138, 3319, 1987
11. M. Kawakami, P. Pekala, M. Lane and A. Cerami: Proc. Natl. Acad. Sci. U.S.A. 79, 912, 1982
12. T. Collins, L. A. Lapierre, W. Fiers, J. L. Strominger and J. S Pober: Proc. Natl. Acad. Sci. U.S.A. 83, 446, 1986
13. G. H. W. Wong and D. V. Goeddel: Nature 323, 819, 1986
14. J. W. Lowenthal, D. W. Ballard, E. B.hnlein and W. C. Greene: Proc. Natl. Acad. Sci. U.S.A. 86, 2331, 1989
15. M. J. Lenardo, C. M. Fan, T. Maniatis and D. Baltimore: Cell 57, 287, 1989
16. A. E. Goldfeld and T. Maniatis: Proc. Natl. Acad. Sci. U.S.A. 86, 1490, 1989
17. A. Waage, A. Halsteuren and T. Espevik: Lancet, Febr. 14, 1987, 355,
18. C. O. Jacob and H. O. McDevitt: Nature 331, 356, 1988
19. G. E. Grau, L. F. Fajardo, P. Piguet, B. Allet, P. Lambert and P. Vassalli: Science 237, 1210, 1987
20. B. Beutler, I. W. Milsark and A. C. Cerami: Science 229, 869, 1985
21. B. B. Aggarwal, T. E. Eessalu and P. E. Hass: Nature 318, 665, 1985
22. M. Tsujimoto, Y. K. Yip and J. Vilcek: Proc. Natl. Acad. Sci. U.S.A. 82, 7626, 1985
23. C. Baglioni, S. McCandless, J. Tavernier and W. Fiers: is J. Biol. Chem. 260, 13395, 1985
24. P. Hohmann, R. Remy, M. Brockhaus and A. P. G. M. van Loon: J. Biol. Chem., im Druck
25. F. C. Kull, S. Jacobs and P. Cuatrecasas: Proc. Natl. Acad. Sci. U.S.A. 82, 5756, 1985
26. A. A. Creasy, R. Yamamoto and Ch. R. Vitt: Proc. Natl. Acad. Sci. U.S.A. 84, 3293, 1987
27. G. B. Stauber, R. A. Aiyer and B. B. Aggarwal: J. Biol. Chem. 263, 19098, 1988
28. K. Hirano, K. Yamamoto, Y. Kobayashi and T. Osawa: J. Biochem. 105, 120, 1989
29. Y. Niitsu, N. Watanabe, H. Sone, H. Neda, N. Yamauchi, M. Maeda and I. Urushizaki: J. Biol. Resp. Modifiers 7, 276, 1988
30. I. Olsson, A. Grubb, U. Gullberg, M. Lantz, E. Nilsson, C. Peetre and H. Thysell: Abstract, 2nd Intern. Conference on Tumor Necrosis Factor and Related Cytokines, Napa, Calif., 15–20 Jan. 1989
31. H. R. Loetscher and M. Brockhaus: Abstract, 2nd Intern. Conference on Tumor Necrosis Factor and Related Cytokines, Napa, Calif., 15–20 Jan. 1989
32. M. Brockhaus, H. Loetscher, H.-P. Hohmann und W. Hunziker: Abstract, 2nd Intern. Conference on Tumor Necrosis Factor and Related Cytokines, Napa, Calif., 15–20 Jan. 1989
33. C. R. Cantor and P. R. Schimmel, in Biophysical Chemistry, W. H. Freeman, ed., San Francisco, 1980, p. 850
34. M. W. Hunkapiller, E. Lujan, F. Ostrander, L. E. Hood: Methods Enzymol. 91, 227, 1983
35. U. K. Lämmli: Nature 227, 680, 1970
36. T. St. John, W. M. Gallatin, M. Siegelman. H. T. Smith, V. A. Fried and I. L. Weissman: Science 231, 845, 1986
37. M. Siegelman, M. W. Bond, W. M. Gallatin, T. St. John, H. T. Smith, V. A. Fried and I. L. Weissman: Science 231, 823, 1986
38. H. Towbin, T. Staehelin and J. Gordon: Proc. Natl. Acad. Sci. U.S.A. 76, 4350, 1979
39. Dinarello, Ch. A., in Lymphokines, Vol. 14, E. Pick, ed., p. 1, Academic Press, London, 1987
40. D. J. Merchant, R. H. Kahn and W. H. Murphy: Handbook of Cell and Organ Culture, Burgess Publ. Co., Minneapolis, 1969
41. G. E. Grau, T. E. Taylor, M. E. Molyneux, J. J. Wirima, P. Vassalli, M. Hommel and P. Lambert: New Engl. J. Med. 320, 1586, 1989
42. J. Sambrook, E. F. Fritsch and T. Maniatis: Molecular Cloning, A Laboratory Manual, 2nd ed., Cold Spring Harbor Laboratory, Cold Spring Harbor, Cold Spring Harbor Laboratory Press, 1989
43. F. M. Ausubel, R. Brent, R. E. Kingston, D. D. Moore, J. A. Smith, J. G. Seidman. and K. Struhl: Current Protocols in Molecular Biology 1987–1988, S. Wiley and Sons, New York, 1987
44. E. Harlow and D. Lane: Antibodies, A Laboratory Manual, Cold Spring Harbor Laboratory Publications, New York, 1988
45. S. Fazekas de St. Groth and D. Scheidegger: J. Immunol. Methods 35, 1, 1980
46. D. Pennica and D. V. Goeddel, in Lymphokines, Vol. 13, D. R. Webb and D. V. Goeddel, eds. p. 163, Academic Press, London, 1987
47. J. Tavernier, L. Franzen, A. Marmenout, J. van der Heyden, R. Muller, M. Ruysschaert, A. van Vliet, R. Banden and W. Fiers, in Lymphokines, Vol. 13, D. R. Webb and D. V. Goeddel, eds., p. 181, Academic Press, London
48. P. J. Fraker and J. C. Speck: Biochem. Biophys. Res. Commun. 80, 849, 1987
49. D. H. Erlich, D. H. Gelfand, R. K. Saiki: Nature 331, 61, 1988
50. Bosserhoff, J. Wallach and R. W. Frank: J. Chromatogr. 473, 71, 1989
51. R. Lathe: J. Mol. Biol. 183, 1, 1985
52. Luckow and Summers, "A Manual of Methods for Baculovirus Vectors and Insect Cell Culture Procedures", Texas Agricultural Experimental Station, Texas A & M University, Bulletin No. 1555, 2nd edition, 1988

We claim:

1. A polynucleotide which consists of the DNA sequence of FIG. 4.

* * * * *